United States Patent [19]

Yamagishi

[11] Patent Number: 4,464,775

[45] Date of Patent: Aug. 7, 1984

[54] METHOD AND APPARATUS FOR COLLECTING X-RAY ABSORPTION DATA IN X-RAY COMPUTED TOMOGRAPHY APPARATUS

[75] Inventor: Yoshio Yamagishi, Utsunomiya, Japan

[73] Assignee: Tokyo Shibaura Denki Kabushiki Kaisha, Japan

[21] Appl. No.: 307,876

[22] Filed: Oct. 2, 1981

[30] Foreign Application Priority Data

Oct. 8, 1980 [JP] Japan ................................ 55-141016

[51] Int. Cl.$^3$ ............................................. G03B 41/16
[52] U.S. Cl. ............................................. 378/5; 378/11
[58] Field of Search ................................... 378/5, 11

[56] References Cited

U.S. PATENT DOCUMENTS

| | | | |
|---|---|---|---|
| 3,924,131 | 12/1975 | Hounsfield | 250/360 |
| 3,946,234 | 3/1976 | Hounsfield | 250/363 S |
| 3,971,948 | 7/1976 | Pfeiler | 378/5 |
| 4,029,963 | 6/1977 | Alvarez | 378/5 |
| 4,066,903 | 1/1978 | LeMay | |
| 4,091,285 | 5/1978 | Logan | 250/360 |
| 4,091,287 | 5/1978 | Hounsfield | |
| 4,103,169 | 7/1978 | Hounsfield | 250/445 T |
| 4,149,031 | 4/1979 | Seppi | 250/445 T |

FOREIGN PATENT DOCUMENTS 1463234 2/1977 United Kingdom .

Primary Examiner—Craig E. Church
Attorney, Agent, or Firm—Finnegan, Henderson, Farabow, Garrett & Dunner

[57] ABSTRACT

In a method of collecting X-ray absorption data in an X-ray tomographic apparatus, an X-ray tube and an X-ray detector arranged to face each other via a body are caused to undergo reciprocation along a plane section of the body for collecting X-ray absorption data of the plane section in a given angular aspect. Two different kinds of X-ray absorption data dependent upon respective different energy levels are collected on the basis of different tube voltage during the respective forward and return movements in one reciprocation. After one reciprocation, the X-ray tube and X-ray detector are rotated by a predetermined angle relative to the body. The reciprocation and rotation are alternately repeated to collect X-ray absorption data of the plane section of the body in various angular aspects. The accuracy of the CT value can be increased using the two different kinds of X-ray absorption data during the forward and backward movements and also the difference between these two X-ray absorption data.

2 Claims, 6 Drawing Figures

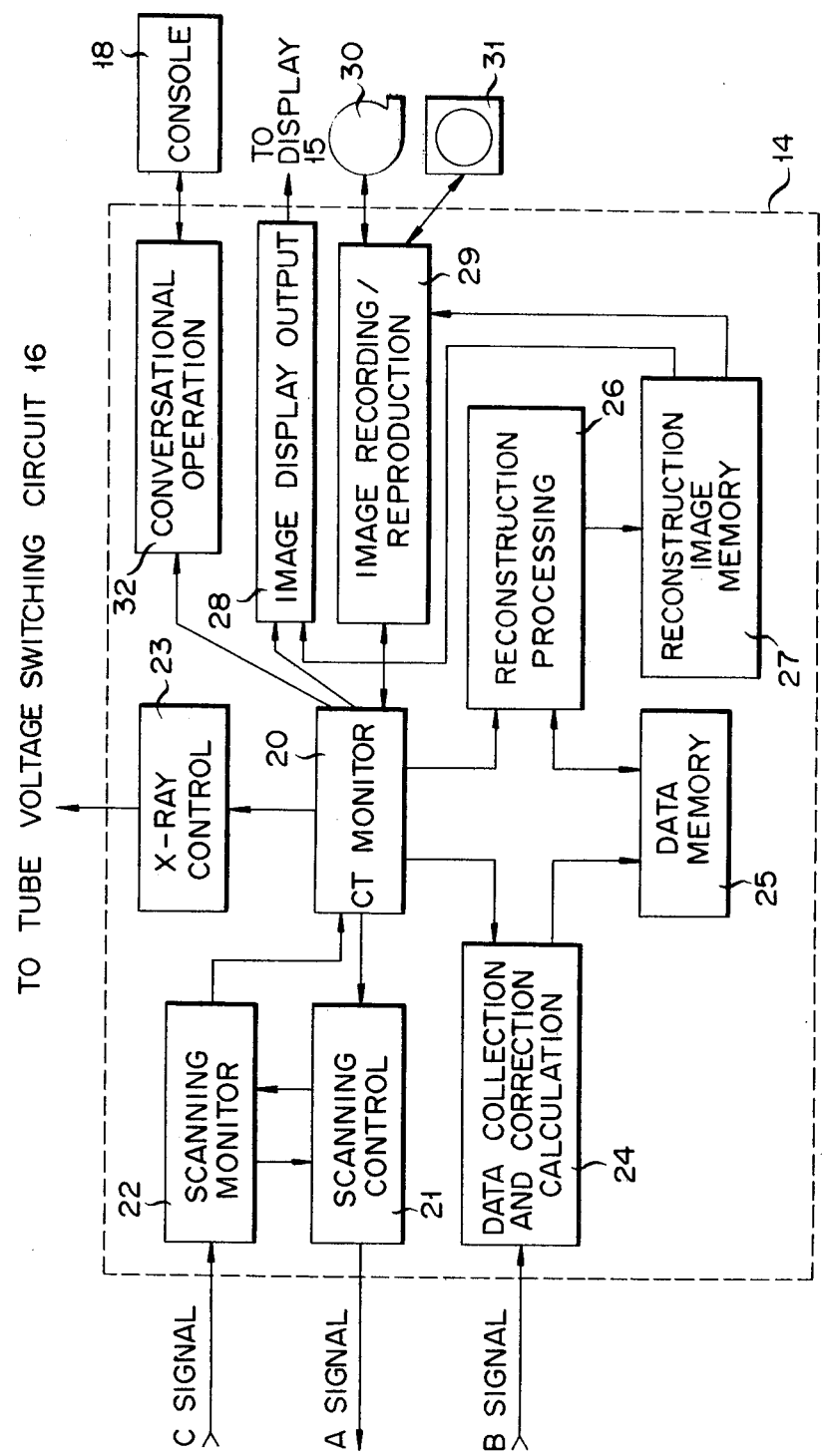

METHOD AND APPARATUS FOR COLLECTING X-RAY ABSORPTION DATA IN X-RAY COMPUTED TOMOGRAPHY APPARATUS

BACKGROUND OF THE INVENTION

This invention relates to method and apparatus for collecting X-ray absorption data in an X-ray computed tomography apparatus, which can obtain precise X-ray absorption data with respect to a given plane section of a patient's body and also permits reconstruction of a high quality tomographic image.

Among X-ray tomographic apparatus, there are computorized tomographic scanners (hereinafter referred to as CT scanner).

One such CT scanner adopts a traverse and rotational system also called a "first generation" system. FIG. 1 shows such a first generation system. In this system, an X-ray tube XT and an X-ray detector DT are disposed to face each other on either side of a patient's body P, and they are traversed together in the direction of the dot-dash arrows in FIG. 1, while the X-ray tube emits X-rays along a plane section of the body P. The x-ray tube XT and the X-ray detector DT being so traversed, a radiation path XR is obtained which is parallel to the plane section of the body P. After one cycle of such scanning is ended, the angle of incidence of X-radiation on the plane section of the body P is changed. The linear motion and rotational motion are alternately repeated as shown in FIG. 2 to collect X-ray absorption data usually over an angle range of 180 degrees. The reconstitution of every point of the plane section of the body P is possible by permitting X-rays to traverse the plane section substantially in all directions or angular aspects.

The X-ray absorption data obtained at the X-ray detector DT is analyzed in an electronic computer to calculate the X-ray absorption factor of individual points of the plane section. A tomographic image is reconstructed through the analysis of each point of the body's plane section on the basis of the determined X-ray absorption factor and with a graduation degree amounting to more than 2,000 steps. In addition to the first generation, there is another traverse and rotational system CT scanner sometime called a "second generation". As shown in FIG. 3, the second generation system uses as the X-ray source an X-ray tube XT which generates X-rays in the form of a sector having a small angle. An X-ray detector DT is disposed to face the X-ray tube XT on the opposite side of the body P as mentioned above. The X-ray detector DT has a plurality of X-ray detecting elements arranged side by side. For the collection of X-ray absorption data, the X-ray tube XT and X-ray detector DT are traversed along a plane section of the body P and, after the completion of traverse scanning in each cycle, rotated by a predetermined angle.

As has been shown, either in the first or second generation the reconstruction of the final image involves image formation through conversion of the value of X-ray absorption that is determined by the structure of the inspected body into a corresponding shade signal. The X-ray absorption factor, i.e., the value of each pixel constituting the image, is referred to as the "CT value". This CT value is linearly related to the X-ray absorption factor and is called the "Hounsfield number" after an early worker in CT technology. This value corresponds to an absorption factor value based on an X-ray energy level of 73 keV (hereinafter referred to as $\mu$ value). Construction of the final image is effected after deriving the CT value. However, the CT value is not an abosolutely definite value for the following reasons. The X-radiation from commercially available CT scanners usually does not consist of a single wavelength at the aforementioned reference energy level of 73 keV but has a spectral distribution. In addition, the X-ray absorption factor M of a predetermined structure of the body is not fixed because of variations of the proportions of the photoelectric effect and Compton effect. More specifically, the X-ray absorption in the neighborhood of a predetermined structure of the body varies depending upon whether or not the structure is surrounded by bones, and an energy spectrum shift, if ay, causes a deviation of the CT value. The X-ray energy distribution which has the most significant influence upon the X-ray absorption value, can be determined by varying the tube voltage of the X-ray tube.

Most existing CT scanners use only a single fixed tube voltage to achieve linear scanning of a plane section of the body. It is therefore necessary to scan the same plane section two or more times, moving the X-ray tube and X-ray detector repeatedly and applying a different voltage on the X-ray tube during each linear scan. This increases the X-ray exposure dose to the patient and requires a longer time, and hence represents a distinct drawback in the system.

It has been contemplated to provide a process for compensating for the shift of the CT value during the signal processing step performed during image construction. However, no correction method that is effective for all bodies and for all scanning conditions has been found.

SUMMARY OF THE INVENTION

An object of this invention is to provide a method and an apparatus for collecting X-ray absorption data in an X-ray tomographic apparatus, in which the collection of X-ray absorption data with respect to a plane section of the body is effected on the basis of different tube voltages during the respective forward and return movements of the X-ray tube and X-ray detector in a reciprocal scanning cycle so that the difference in the absorption value between the forward and return strokes of the scan may be used for correcting the deviation of the CT value, to thereby increasing the accuracy of the system.

To attain this object, the method and apparatus for collecting X-ray absorption data according to the invention comprises the steps of collecting X-ray absorption data of a given plane section of a body while an X-ray tube and a X-ray detector disposed to face the X-ray tube scan said plane section in a first direction while a first voltage is applied to the X-ray tube, collecting X-ray absorption data of the plane section while the X-ray tube and X-ray detector are moving in a second direction opposite to the first direction while a second voltage different from the first voltage is applied to the X-ray tube, rotating the body relative to the X-ray tube and X-ray detector by a predetermined angle; and repeating the first and second collecting steps and the rotating step until the body is rotated relative to the X-ray tube and X-ray detector through at least 180°.

Also, the apparatus for collecting X-ray absorption data in an X-ray computed tomography apparatus according to the invention comprises computer means for effecting operations of at least supplying a scanning start signal to an X-ray tube and also to an X-ray detector, receiving a signal indicative of the direction of scanning of the X-ray tube and X-ray detector, generating a tube voltage switching instruction signal at the time of changing the scanning direction, receiving X-ray absorption data detected by the X-ray detector during the forward and return traverses of scanning and also providing an image reconstruction output to a display unit and also generating energy-dependent diagonsis data from the two different energy data obtained during the forward and return traverses of scanning respectively, means connected to the X-ray tube for supplying a tube voltage thereto, and tube voltage switching control means connected between the X-ray tube and the tube voltage supplying means for controlling the switching of different tube voltages for the respective forward and return traverses in the reciprocal scanning of the X-ray tube and X-ray detector according to a tube voltage switching instruction signal received from the computer means.

With the above method and apparatus for collecting X-ray absorption data in an X-ray computed tomography apparatus according to the invention, two different kinds of X-ray absorption data with respect to a given plane section of the body which are respectively based on the two different tube voltages, can be collected in a short period of time, and a highly accurate image with the CT value close to the characteristics of the structure of the body can be obtained from three different kinds of X-ray absorption data, namely two based upon the two different tube voltage and the last one as the difference between these two different data.

BRIEF DESCRIPTION OF THE DRAWINGS

FIG. 6 is a block diagram illustrating the function of the computer shown in FIG. 5.

DETAILED DESCRIPTION OF THE PREFERRED EMBODIMENT

Figure 1:
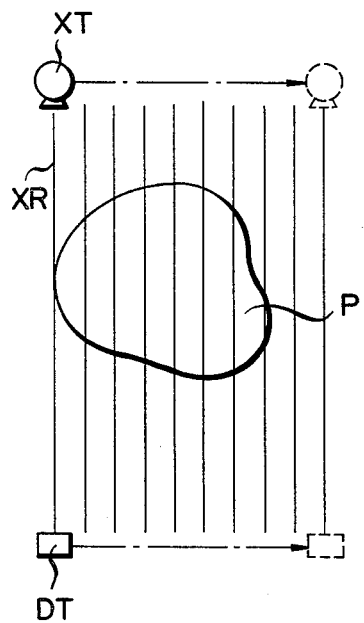
FIG. 1 is a schematic diagram illustrating the scanning operation of a prior art first generation CT scanner system.
Figure 2:
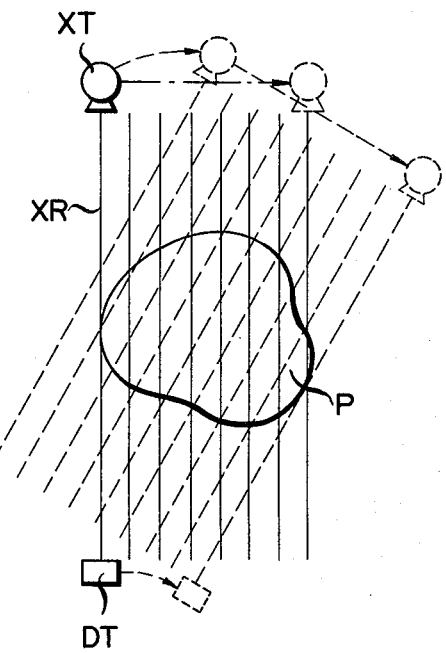
FIG. 2 is a schematic diagram illustrating the rotational operation of the prior art CT scanner shown in FIG. 1.
Figure 3:
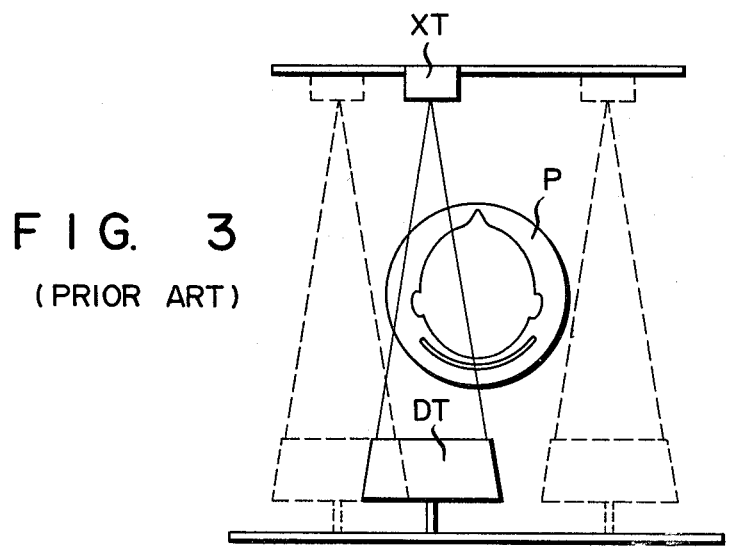
FIG. 3 is a schematic diagram illustrating the traverse operation of a prior art second generation CT scanner.
Figure 4:
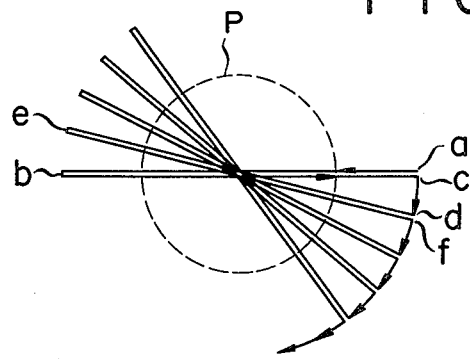
FIG. 4 is a schematic diagram illustrating the orbit of motion of an X-ray tube and implementing the method of collecting X-ray absorption data according to the invention.
Figure 5:
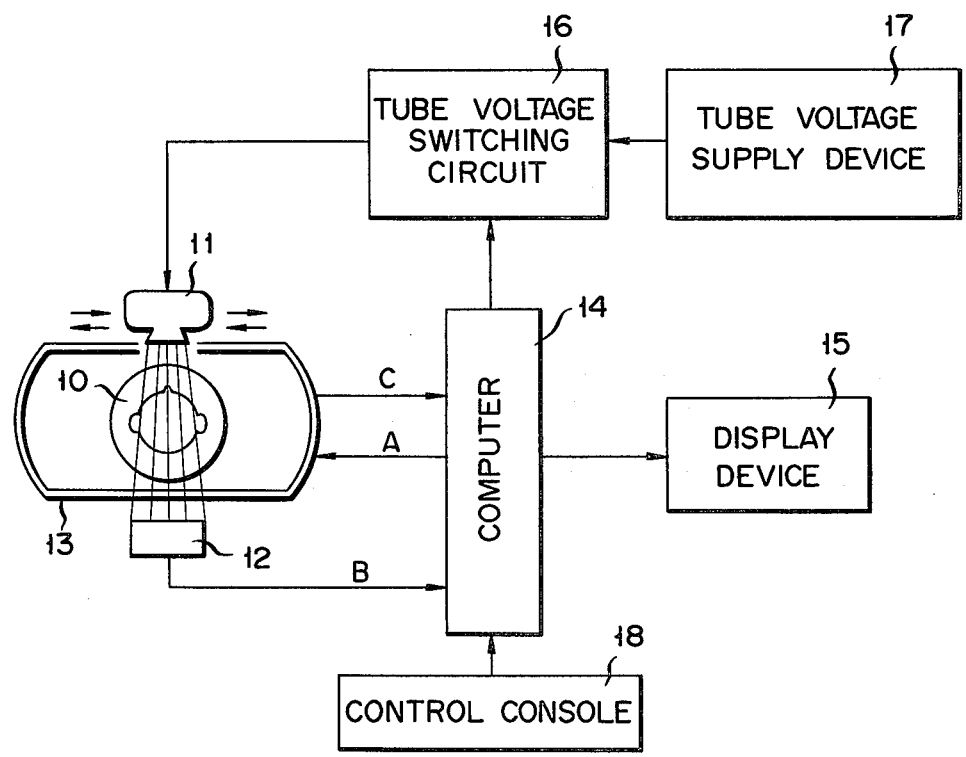
FIG. 5 is a schematic block diagram outlining an X-ray absorption data collection apparatus in an X-ray tomographic apparatus according to the invention.

Now, an embodiment of the invention will be described with reference to FIGS. 4, 5 and 6.

The invention, in the embodiment illustrated, may be applied to a first generation and a second generation CT scanner. FIG. 4 shows the orbit of movement of an X-ray tube and an X-ray detector disposed to face each other via a body.

The X-ray tube and X-ray detector which are located at a position "a" are linearly traversed forward to scan the body P with the X-ray tube emitting X-rays on the basis of a predetermined tube voltage, for instance 100 kV. In the backward or return traverse, the X-ray detector detects X-ray absorption data in a plane section of the body P in a given angular aspect. When the X-ray tube reaches a point "b", its voltage is switched to, for instance, 140 kV. Then, the X-ray tube and X-ray detector return to the point c. During their return traverse, X-ray absorption data is obtained on the basis of a different tube voltage from that during the forward traverse. Thus, two different kinds of X-ray absorption data are obtained with respect to the same plane section. Then, the X-ray tube and X-ray detector at the point c are rotated by a predetermined angle to a point d. When the point d is reached, the X-ray tube voltage is again switched to the aforementioned predetermined voltage, and during the subsequent forward traverse up to the point e X-ray absorption data is detected with respect to the X-rays that are emitted from the X-ray tube toward the body P on the basis of the aforementioned predetermined tube voltage. Upon reaching of the point e, the tube voltage is switched once again, and X-ray absorption data is detected on the basis of the different tube voltage from that during the forward traverse until the X-ray tube and X-ray detector arrive at a point f. The sequence of linear motion and rotational motion as mentioned are repeated, and the detection of X-ray absorption data with respect to a given plane section is ended with the completion of 180-degree rotation. It is noted that FIG. 4 is a schematic representation only and that the actual paths followed by the X-ray tube do not pass through the center of the body P, but rather are offset from the center of the scan such that the midpoints of the scan paths are tangent to a circle circumscribing the body P.

The detection or collection of data on the basis of two different tube voltages, one during the forward traverse and the other during the return traverse in the illustrated translational reciprocal scan pattern, permits obtaining three different images, namely two images based on the respective tube voltages during the forward and return traverses and an image obtained by correction with the difference between the X-ray absorptions based on the two different tube voltages. Thus, an image having at CT value close to the structure of the body can be obtained. Particularly, it is possible to make analysis of the X-rays' electron density and the structural element composition of the body from the aforementioned X-ray absorption difference data.

Now, an X-ray absorption data collection apparatus according to the invention will be described with reference to FIG. 5.

An X-ray tube 11 and an X-ray detector 12 are supported by a frame 13 such that they face each other via a body 10. The X-ray tube 11 and X-ray detector 12 are capable of both linear motion and rotational motion with respect to the body 10.

A start instruction to start the scanning of the X-ray tube and X-ray detector 12, a scanning speed switching instruction and/or a slice width switching instruction are supplied as control instruction signal A from a computer 14 to the CT scanner.

The aforementioned two different sets of X-ray absorption data based on the different tube voltages, detected by the X-ray detector 12, are coupled as data detection signal B to the computer 14. In the computer 14, the data detection signal B is analyzed for display of the reconstruction image on a display unit 15 at a graduation degree corresponding to X-ray absorption factor at each point of the plane section.

A signal C which indicates whether the X-ray tube 11 and X-ray detector 12 are in their forward or return travel is also coupled to the computer 14. A tube voltage supply device 17 is connected through a tube voltage switching circuit 16 to the X-ray tube 11. The tube voltage switching circuit 16 is connected to the computer 14. When the computer 14 detects the end of the forward or return traverse from the aforementioned signal C from the CT scanner, it supplies a control signal to the tube voltage switching circuit 16 to switch the tube voltage supplied from the tube voltage supply device 17 to the X-ray tube 11. The setting of the computer 14 in accordance with the system condition of the CT scanner is done from a control console 18. The function of the computer 14 will now be described with reference to the block diagram of FIG. 6.

A scanning control circuit 21 generates the instruction signal A supplied to the CT scanner according to an instruction signal from a CT monitor 20. A scanning monitor 22 detects the aforementioned signal C from the CT scanner, indicating the state of motion of the X-ray tube 11 and X-ray detector 12, and reports the detection to the CT monitor 20. After confirming the scanning state of the CT scanner, the CT monitor 20 gives an instruction to an X-ray control circuit 23 to let the control circuit 23 supply a control signal to the tube voltage switching circuit 16 mentioned above according to the detected scanning state. A data collection and correction calculation circuit 24 collects the X-ray detection data signal B corresponding to the affected part of the body 10, detected by the X-ray detector 12 mentioned above, and effects correction calculation with the detection data signal B in accordance with an instruction supplied from the CT monitor 20. The result of the calculation is stored in a data memory 25. A reconstruction signal processing circuit 26 receives the stored data output from the data memory 25 and an instruction output from the CT monitor 20 and reconstruct the X-ray detection data. The reconstruction data is stored in a reconstruction image memory 27. An image display output circuit 28 receives the stored data from the reconstruction image memory 27 and an instruction signal from the CT monitor 20 and supplies an image display output to the image display unit 15 mentioned above for display. An image recording/reproducing circuit 29 receives the stored data from the reconstruction image memory 27 and an instruction signal from the CT monitor 20 and forwards the received reconstruction image data for storage magnetic on a tape 30 or on a floppy disc 31.

The CT monitor 20 is connected through a conversation operation circuit 32 to the console 18 mentioned above. The conversation operation circuit 32 controls the operation procedure depending upon the condition of the CT system under the control of an instruction signal from the control console 18.

What is claimed is:

1. A method of collecting X-ray absorption data in an X-ray computed tomography apparatus, comprising the steps of:
   collecting X-ray absorption data of a given plane section of a body while an X-ray tube and an X-ray detector disposed to face said X-ray tube scan said plane section in a first direction while a first voltage is applied to said X-ray tube;
   collecting X-ray absorption data of said plane section while said X-ray tube and X-ray detector are moving in a second direction opposite to said first direction while a second voltage different from said first voltage is applied to said X-ray tube;
   rotating said body relative to said X-ray tube and X-ray detector by a predetermined angle; and
   repeating said first and second collecting steps and said rotating step until said body is rotated relative to said X-ray tube and X-ray detector through at least 180°.

2. Apparatus for collecting X-ray absorption data in a computed tomography apparatus comprising:
   projection means for generating X-radiation and projecting said radiation through a body;
   detection means for detecting a beam of said projected X-radiation after it has passed through said body and producing absorption data output signals in response to said beam;
   drive means for synchronously moving said projection and detection means along parallel paths to scan said X-radiation through a plane section of said body, said moving means being constructed and arranged to move said projection and detection means in a sequence of reciprocating forward and reverse traversals of their respective paths;
   means for pivoting said projection and detection means through a predetermined angle after each cycle of forward and reverse scanning movement whereby each said cycle of reciprocating movement is effected at a different angle relative to said body;
   voltage means included in said projection means for changing the voltage level at which said X-radiation is generated;
   control means for controlling said voltage means to shift said X-ray generation voltage between first and second levels in synchronism with the operation of said drive means such that during each forward traversal of said projection means said voltage is set at said first level and during each reverse traversal of said projection means, said voltage is set at said second level; and
   means for receiving and processing said absorption data output signals to construct a tomographic image of said body.

* * * * *